US012558564B2

(12) United States Patent
Jo et al.

(10) Patent No.: US 12,558,564 B2
(45) Date of Patent: Feb. 24, 2026

(54) CAP DEVICE FOR SCALP CARE

(71) Applicant: Access Business Group International LLC, Ada, MI (US)

(72) Inventors: Hae Jo, Hanam City (KR); Soha Jeon, Seoul (KR)

(73) Assignee: Access Business Group International LLC, Ada, MI (US)

( * ) Notice: Subject to any disclaimer, the term of this patent is extended or adjusted under 35 U.S.C. 154(b) by 251 days.

(21) Appl. No.: 18/289,959

(22) PCT Filed: May 12, 2022

(86) PCT No.: PCT/KR2022/006801
§ 371 (c)(1),
(2) Date: Nov. 8, 2023

(87) PCT Pub. No.: WO2022/255684
PCT Pub. Date: Dec. 8, 2022

(65) Prior Publication Data

US 2024/0245928 A1      Jul. 25, 2024

(30) Foreign Application Priority Data

Jun. 3, 2021    (KR) ........................ 10-2021-0071927

(51) Int. Cl.
*A61N 5/06* (2006.01)
*A61N 5/00* (2006.01)
*A61N 5/067* (2006.01)

(52) U.S. Cl.
CPC ........... *A61N 5/0617* (2013.01); *A61N 5/067* (2021.08); *A61N 2005/007* (2013.01);
(Continued)

(58) Field of Classification Search
CPC .................. A61N 5/0617; A61N 5/067; A61N 2005/007; A61N 2005/0647;
(Continued)

(56) References Cited

U.S. PATENT DOCUMENTS 5,950,245 A * 9/1999 Binduga ................ A42B 3/145
24/68 B
10,112,058 B2 * 10/2018 Hamid ................. A61N 5/0617
(Continued)

FOREIGN PATENT DOCUMENTS

KR      20120127814 A      11/2012
KR      20150002357 A      1/2015
(Continued)

*Primary Examiner* — Jonathan T Kuo
(74) *Attorney, Agent, or Firm* — Warner Norcross + Judd LLP

(57)      ABSTRACT

A cap device for scalp care is provided. The cap device includes an interior cover, an exterior cover coupled to the interior cover, a substrate, and a blower. The interior cover covers the scalp, and has emitting holes for emitting air. The exterior cover defines an air flow passage along the interior cover, and has a vent hole for sucking air. The substrate is coupled to the interior cover in the air flow passage to cover an outer surface of the interior cover. The substrate has laser diodes, infrared ray and red light emitting diodes, and through holes corresponding to the emitting holes. The blower communicates with the air flow passage at an upper end of the interior cover. The blower sucks air through the vent hole and emits the air to the scalp through the emitting holes via the air flow passage.

12 Claims, 10 Drawing Sheets

(52) U.S. Cl.
CPC ................. *A61N 2005/0647* (2013.01); *A61N 2005/0652* (2013.01); *A61N 2005/0659* (2013.01); *A61N 2005/0663* (2013.01)

(58) Field of Classification Search
CPC .... A61N 2005/0652; A61N 2005/0659; A61N 2005/0663; A61N 5/00; A61N 2005/0626; A61N 5/06–2005/073; A61F 7/00; A61F 7/0085; A61F 2007/0008; A61F 2007/006; A61F 2007/0063; A61B 18/20–18/28

See application file for complete search history.

(56) References Cited

U.S. PATENT DOCUMENTS

| | | | |
|---|---|---|---|
| 10,688,315 B2 * | 6/2020 | Medendorp, Jr. .... | A61N 5/0616 |
| 2010/0106077 A1 * | 4/2010 | Rabin ................. | A61N 5/0617 |
| | | | 604/20 |
| 2014/0296946 A1 * | 10/2014 | Malek ................. | A61N 5/0617 |
| | | | 607/89 |
| 2017/0028216 A1 * | 2/2017 | Medendorp, Jr. .... | A61N 5/0616 |
| 2018/0008839 A1 * | 1/2018 | Hamid ................. | A61N 5/0617 |

FOREIGN PATENT DOCUMENTS

| | | | | | |
|---|---|---|---|---|---|
| KR | 101803867 B1 | * | 12/2017 | .......... | A61N 5/0616 |
| KR | 20200015149 A | * | 2/2020 | .............. | A61F 7/00 |
| KR | 102209429 B | | 1/2021 | | |
| WO | 9846097 A1 | | 10/1998 | | |

* cited by examiner

FD ← → RD

CAP DEVICE FOR SCALP CARE

TECHNICAL FIELD

The present disclosure relates to a cap device that can be worn on a scalp for scalp care.

BACKGROUND

It is known that low-intensity laser light, referred to as a low-level laser therapy (LLLT), promotes repair and regeneration of biological tissues, and activates cell activity. Further, data showing that the low-level laser therapy enhances hair growth and delays progression of hair loss has been clinically proven.

Accordingly, a laser hair loss treatment device, which is configured to irradiate laser light based on the low-level laser therapy to a scalp, is commercially available. Such a laser hair loss treatment device has a helmet form or a cap form so as to be worn on a user's head.

Heat is applied to the scalp due to the laser light irradiated by the laser hair loss treatment device. The heat applied to the scalp may become another cause of hair loss. However, the conventional laser hair loss treatment device is only designed to be suitable for a laser light irradiating structure, and cannot remove the heat applied to the scalp. Further, the conventional laser hair loss treatment device is not designed so as to take user convenience and user safety into consideration.

SUMMARY

Embodiments disclosed herein provide a cap device for scalp care that solves the aforementioned problems of the prior art. One embodiment of the present disclosure provides a cap device for scalp care, which can irradiate laser light to a scalp by means of a low-level laser therapy and can lower a temperature of the scalp. One embodiment of the present disclosure provides a cap device for scalp care which enhances user convenience by adjusting the size of a wearing space. One embodiment of the present disclosure provides a cap device for scalp care which enhances user safety by irradiating laser light only in the wearing state.

The disclosed embodiments relate to a cap device which is wearable on a scalp of a head for scalp care. The cap device for scalp care of one embodiment includes an interior cover, an exterior cover, a substrate, and a blower. The interior cover is formed to cover the scalp, is composed of a transparent material, and has a plurality of emitting holes for emitting air to the scalp. The exterior cover is coupled to the interior cover. The exterior cover is configured to define an air flow passage along an outer surface of the interior cover, and has a vent hole for sucking air from an outside. The substrate is coupled to the interior cover in the air flow passage to cover the outer surface of the interior cover. The substrate has a plurality of laser diodes and a plurality of infrared ray and red light emitting diodes, which irradiate light to the scalp, and a plurality of through holes corresponding to the plurality of emitting holes. The blower is disposed in a position of an upper end of the interior cover to communicate with the air flow passage. The blower is configured to suck air through the vent hole and to emit the air to the scalp through the plurality of emitting holes via the air flow passage.

In one embodiment, the interior cover has a plurality of protruding portions protruding toward the exterior cover, and at least a portion of the plurality of emitting holes is formed in and perforated through the plurality of protruding portions. The plurality of protruding portions may be arranged in a plurality of rows in the interior cover.

In one embodiment, the interior cover has a pair of positioning protrusions protruding from the outer surface in the vicinity of the upper end, and the substrate has positioning holes to which the pair of positioning protrusions are fitted respectively. The blower is disposed between the pair of positioning protrusions.

In one embodiment, the interior cover and the exterior cover are configured such that the air flow passage gradually narrows from the upper end of the interior cover toward a lower end of the interior cover.

In one embodiment, each of the interior cover and the exterior cover has a brim portion protruding in a frontward direction of the head, and the brim portion of the interior cover and the brim portion of the exterior cover have a corresponding shape.

In one embodiment, the substrate includes a base portion positioned on the upper end of the interior cover, and a plurality of arm portions extending from the base portion and bendable toward the interior cover. The arm portions, which are neighboring in a circumferential direction of the interior cover among the plurality of arm portions, are formed to define one through hole among the plurality of through holes. The neighboring arm portions are configured to be separably coupled to each other.

In one embodiment, the cap device for scalp care further includes a gap adjustment device, which is coupled to the interior cover and is configured to adjust a gap between the interior cover and the scalp in a frontward direction and a rearward direction of the head.

In one embodiment, the gap adjustment device includes a pair of bands, a housing, and an adjustment dial. Each of the pair of bands has one end portion removably coupled to the interior cover and an opposite end portion formed with a rack gear, and the pair of bands are disposed in a circumferential direction of the interior cover. The housing is configured to accommodate the opposite end portions of the pair of bands such that the opposite end portions are slidable in opposite directions, and the housing is in contact with a back of the head. The adjustment dial has a pinion gear disposed between and meshing with the rack gears of the pair of bands, and is rotatably coupled to the housing. The housing may have a plurality of detent teeth disposed in an annular shape about a rotation axis of the adjustment dial, and the adjustment dial may have a ratchet plate coupled to the pinion gear and having a ratchet tooth meshing with one of the detent teeth. The ratchet tooth may sequentially mesh with the plurality of detent teeth as the adjustment dial is rotated.

In one embodiment, the cap device for scalp care further includes: a control device configured to control an operation of the laser diodes, an operation of the infrared ray and red light emitting diodes, and an operation of the blower: and an electrical power source supplying electrical power to the laser diodes, the infrared ray and red light emitting diodes, and the blower.

In one embodiment, the cap device for scalp care further includes a wearing detection sensor, which is disposed in the interior cover and is configured to detect a state where the interior cover is worn on the scalp. The control device is configured to stop the operations of the plurality of laser diodes and the plurality of infrared ray and red light emitting diodes when the wearing detection sensor detects that the scalp does not exist in the interior cover.

The cap device for scalp care according to one embodiment not only irradiates laser light to the scalp, but also emits air in the form of wind to the scalp. Thus, the cap device for scalp care according to one embodiment can realize prevention of hair loss and promotion of hair growth by a low-level laser therapy while effectively removing the heat generated in the scalp by the laser light. Further, the cap device for scalp care according to one embodiment can adjust the gap between the interior cover and the scalp by the gap adjustment device. Therefore, the cap device for scalp care according to one embodiment can be easily applied to various head sizes and can enhance user convenience. Further, the cap device for scalp care according to one embodiment can detect the state of being worn on a scalp, and can stop the operation of the diodes when the cap device is not worn on the scalp. Therefore, the cap device for scalp care according to one embodiment irradiates light from the diodes to the scalp only in the wearing state, and can thereby enhance user safety.

DETAILED DESCRIPTION

Figure 1:
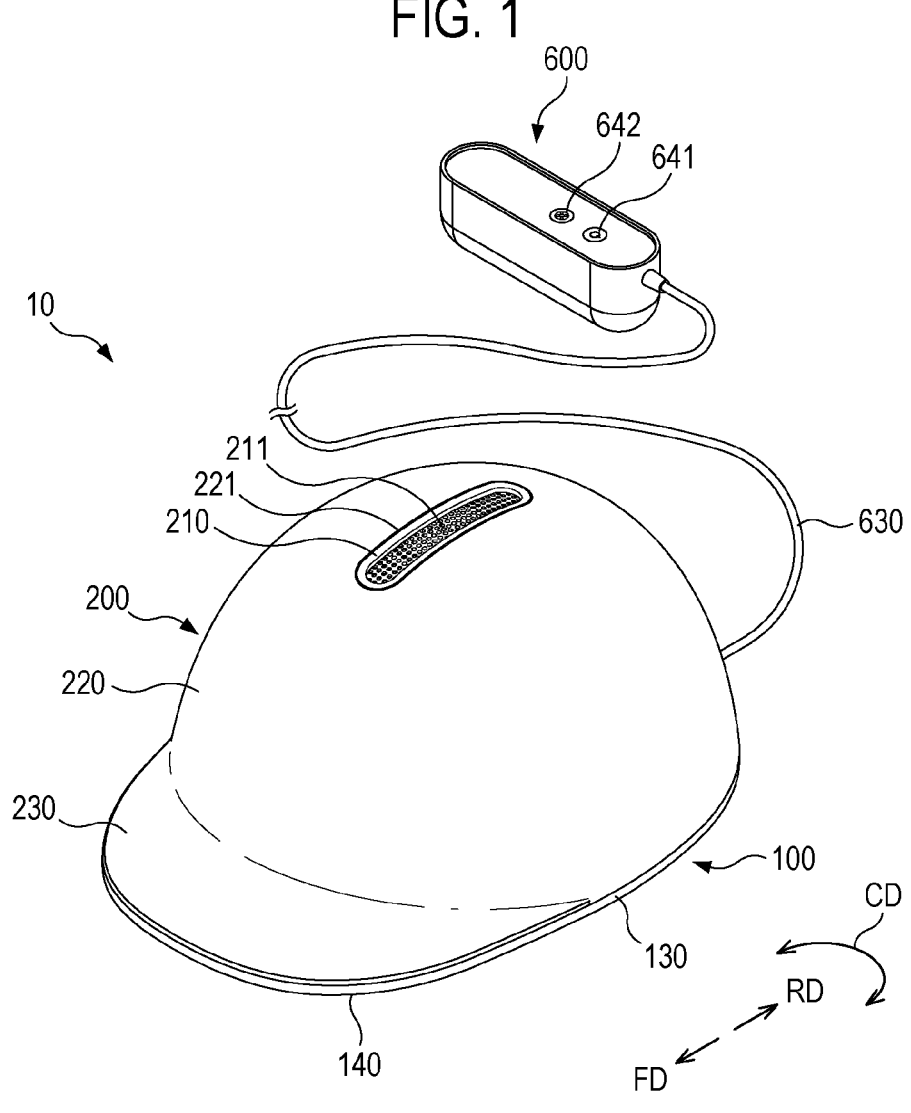
FIG. 1 is a perspective view showing a cap device for scalp care according to one embodiment.

Embodiments of the present disclosure are illustrated for the purpose of explaining the technical idea of the present disclosure. The scope of the rights according to the present disclosure is not limited to the embodiments presented below or the detailed descriptions of such embodiments.

All technical terms and scientific terms used in the present disclosure include meanings that are commonly understood by those of ordinary skill in the technical field to which the present disclosure pertains unless otherwise defined. All terms used in the present disclosure are selected for the purpose of describing the present disclosure more clearly, and are not selected to limit the scope of the rights according to the present disclosure.

Expressions such as "comprising," "including," "having," and the like used in the present disclosure are to be understood as open-ended terms having the possibility of encompassing other embodiments, unless otherwise mentioned in the phrase or sentence containing such expressions.

Singular expressions that are described in the present disclosure may encompass plural expressions unless otherwise stated, which will also apply to the singular expressions recited in the claims.

Expressions such as "first," "second," etc. used in the present disclosure are used to separate a plurality of elements from each other, and are not intended to limit an order or importance of the elements.

In the present disclosure, the description that one element is "connected" or "coupled" to another element should be understood to indicate that the aforesaid one element may be directly connected, or coupled, to the aforesaid another element, and should be further understood that the aforesaid one element may be connected or coupled to the aforesaid another element via a new element.

The dimensional and numerical values described in the present disclosure are not limited only to the dimensional and numerical values described herein. Unless specified otherwise, the dimensional and numerical values may be understood to mean the described values and equivalent ranges including the values.

The directional term "frontward" used in the present disclosure means a direction directed from the back of a head toward the front of the head, and the directional term "rearward" means a direction opposite to the frontward direction. The directional terms "upward," "upper" and the like used in the present disclosure and the directional terms "downward," "lower" and the like used in the present disclosure are based on an orientation shown in the accompanying drawings.

Hereinafter, the embodiments are described with reference to the accompanying drawings. Like reference numerals in the accompanying drawings denote like or corresponding elements. Further, in the following description of the embodiments, redundant descriptions for the same or corresponding elements may be omitted. However, even if the descriptions of the elements are omitted, such elements are not intended to be excluded in any embodiment.

The embodiments disclosed below and the embodiments shown in the accompanying drawings are directed to a cap device that can be used for scalp care, such as repair and regeneration of scalp tissues and delay and prevention of hair loss. The cap device for scalp care (hereinafter, simply referred to as a "cap device") according to the embodiments may be used in a state of being worn on the scalp of a user's head.

The cap device according to one embodiment is formed to cover the scalp of a head in accordance with the shape of the scalp. The cap device is configured to irradiate laser light, red light, and near-infrared ray light toward the scalp. Further, the cap device is configured to emit air in the form of wind to the scalp while irradiating the laser light, the red light, and the near-infrared ray light. Therefore, by the aforementioned light, the cap device according to one embodiment can promote repair and regeneration of tissues constituting the scalp, and can activate cell activity of the scalp tissues. Further, by emitting air in the form of wind to the scalp, the cap device according to one embodiment can lower the temperature of the scalp and can remove the heat of the scalp.

Figure 2:
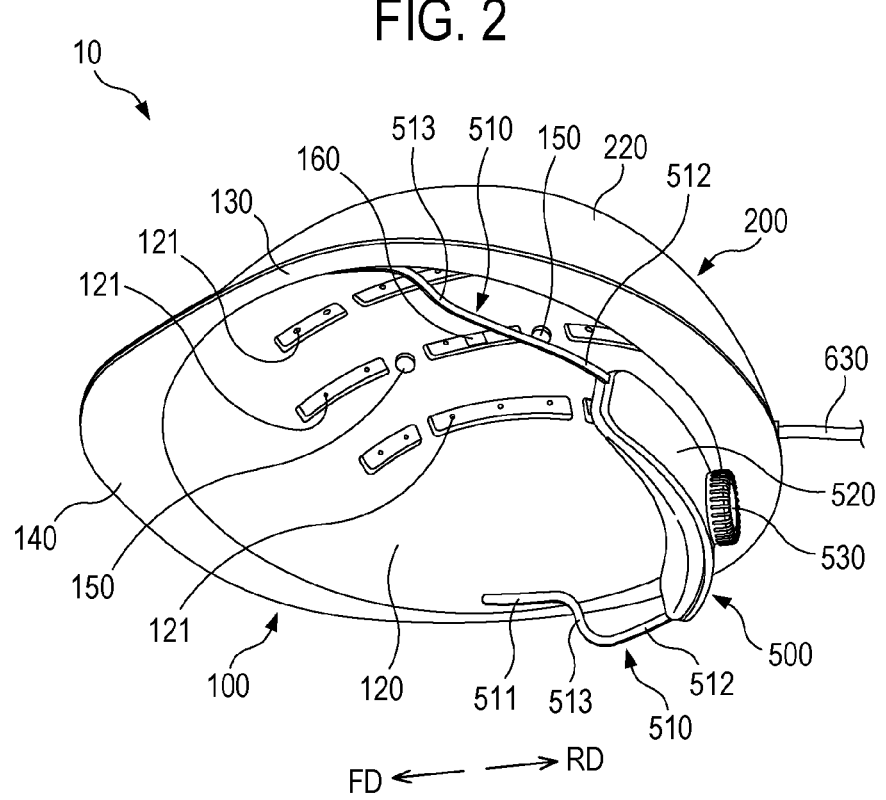
FIG. 2 is another perspective view showing the cap device for scalp care according to one embodiment.
Figure 3:
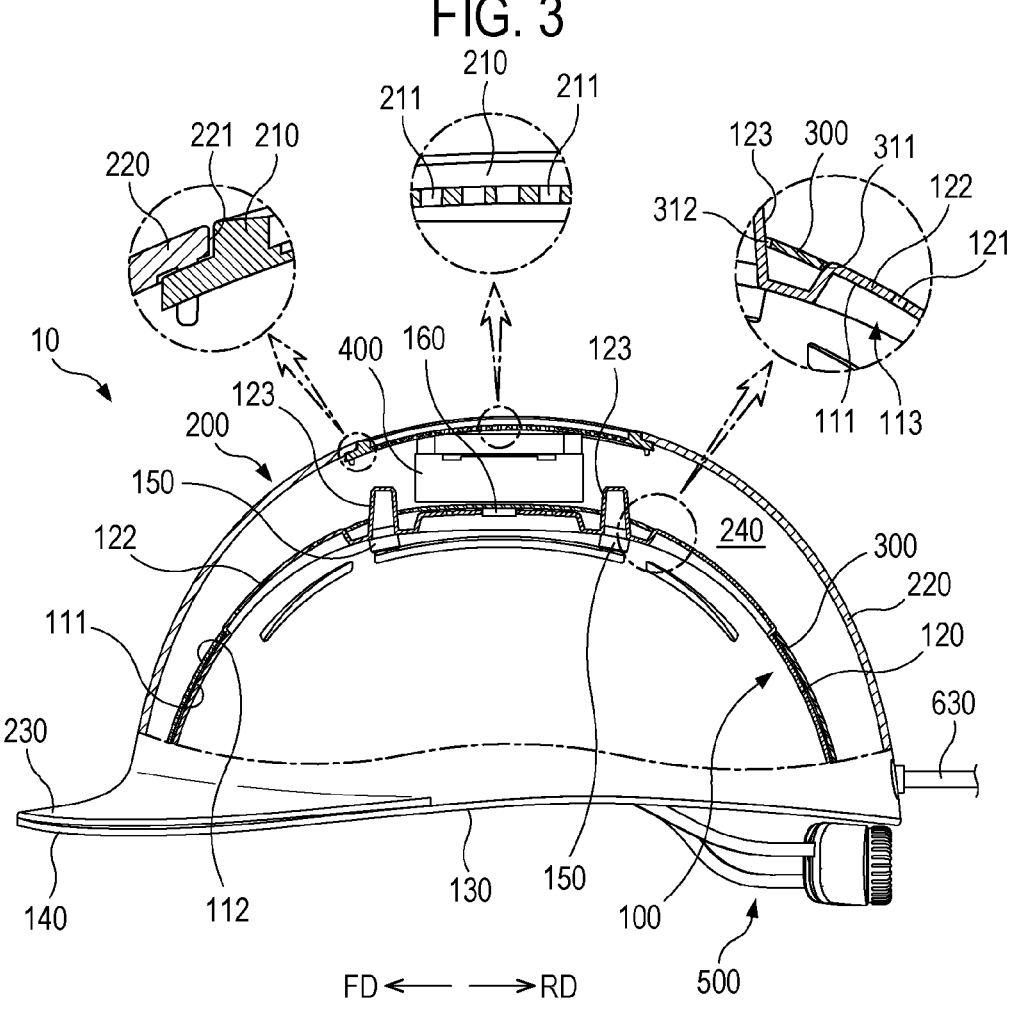
FIG. 3 is a cross-sectional view showing the cap device for scalp care according to one embodiment.

FIGS. 1 and 2 are perspective views showing a cap device according to one embodiment. FIG. 3 is a cross-sectional view showing the cap device according to one embodiment. Reference is made to FIGS. 1 to 3.

The cap device 10 according to one embodiment includes an interior cover 100 covering the scalp of a head in accordance with the shape of the scalp, and an exterior cover 200 functioning as an exterior member of the cap device 10. Further, the cap device 10 includes a substrate 300 disposed between the interior cover 100 and the exterior cover 200, and a blower 400 emitting air. A plurality of diodes that irradiate laser light, red light, and near-infrared ray light are mounted on the substrate 300. The blower 400 sucks air from the outside of the cap device and emits the air.

Figure 4:
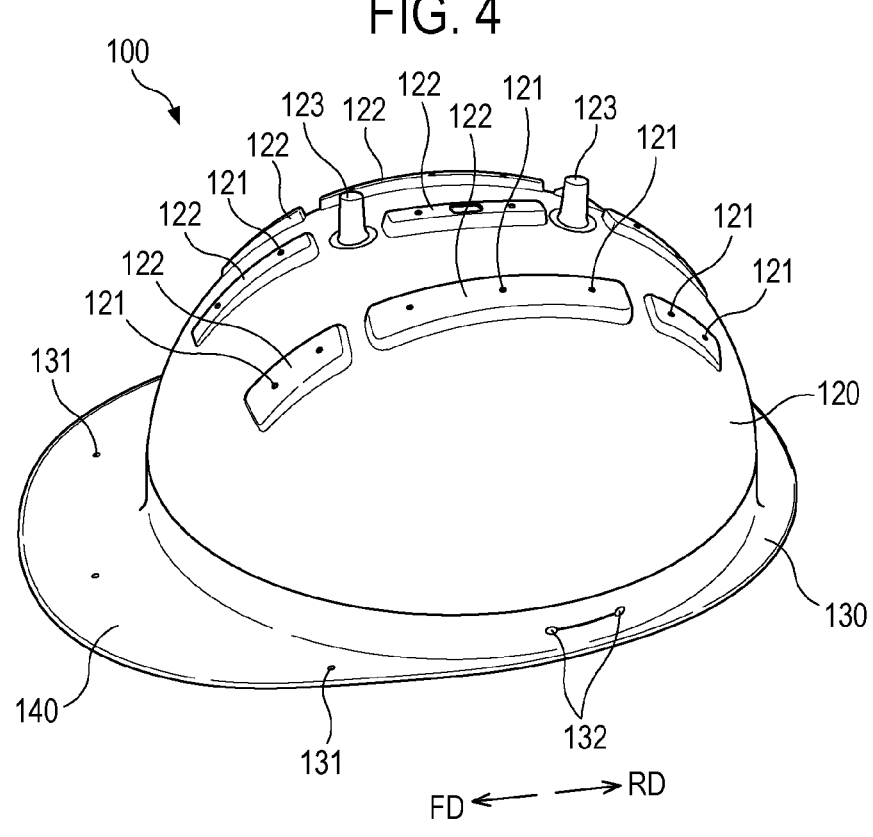
FIG. 4 is a perspective view showing an interior cover of the cap device according to one embodiment.

FIG. 4 is a perspective view showing the interior cover of the cap device according to one embodiment. Reference is made to FIGS. 2 to 4.

The interior cover 100 is formed to cover a scalp. The interior cover 100 may be formed by injection molding to have a substantially hemispherical shape. A portion or the entirety of the interior cover 100 may be composed of a transparent material, for example, a transparent plastic material. Thus, the laser light, the red light, and the near-infrared ray light from the substrate can be irradiated to the scalp through the interior cover 100.

The interior cover 100 has an inner surface 111, which becomes a surface located at a side facing the scalp, and an outer surface 112, which is located opposite to the inner surface 111 in a thickness direction of the interior cover and faces the exterior cover 200. Further, the interior cover 100 has a cover portion 120, which covers the scalp and is formed in a substantially hemispherical shape, and a coupling flange 130 formed along a lower edge of the cover portion 120. An inner surface of the cover portion 120 can become the inner surface 111 of the interior cover 100. An outer surface of the cover portion 120 can become the outer surface of the interior cover, which is opposite to the inner surface of the interior cover. A front portion of the coupling flange 130 protrudes further in the frontward direction FD than the remaining portion of the coupling flange 130, thereby forming a portion that a user can recognize as a brim. That is, the interior cover 100 has a brim portion 140 protruding in the frontward direction FD. A plurality of through holes 131 are formed in the coupling flange 130. Screws are fastened to the exterior cover 200 through the through holes 131, respectively, and therefore the screws can couple the interior cover 100 and the exterior cover 200 along the edges thereof. As another example, the cover portion 120 may be composed of the aforementioned transparent plastic material, and the coupling flange 130 may be composed of a translucent or opaque plastic material.

The interior cover 100 has a plurality of emitting holes 121 for emitting air to the scalp. The air may be emitted and supplied to the scalp in the form of wind through the emitting holes 121. The plurality of emitting holes 121 are formed to be perforated through the interior cover 100 in the thickness direction of the interior cover. In the interior cover 100, the plurality of emitting holes 121 may be arranged in a plurality of rows extending from the forehead of the head up to the back of the head. According to one embodiment, the interior cover 100 has, in the cover portion 120, a plurality of protruding portions 122 that protrude toward the exterior cover 200. At least a portion of the plurality of emitting holes 121 are formed in and perforated through the plurality of protruding portions 122 in the thickness direction of the interior cover.

A portion of the inner surface 111 in the protruding portion 122 is located more outward than the other portion of the inner surface 111 except the protruding portion 122. Therefore, a portion of the inner surface 111 of the interior cover 100 is recessed toward the exterior cover 200 in the region of the protruding portion 122, and a groove 113 is formed in the inner surface 111 in the region of the protruding portion 122. Such a groove 113 provides a clearance space between the inner surface 111 of the interior cover and the scalp. Accordingly, the air, which is emitted through the emitting holes 121 of the protruding portion 122, is smoothly diffused through the aforementioned clearance space and can be supplied to the scalp.

Each protruding portion 122 is formed in a rectangular shape having a predetermined width and length, and extends in the frontward direction FD and the rearward direction RD. Further, the plurality of protruding portions 122 are arranged in a plurality of rows in the cover portion 120 of the interior cover. According to one embodiment, the plurality of protruding portions 122 are arranged in three rows parallel to one another in the cover portion 120. The rows formed by the plurality of protruding portions are located in the frontward direction FD and the rearward direction RD. That is, the rows formed by the plurality of protruding portions are located in the frontward direction FD and the rearward direction RD so as to extend from the forehead of the head up to the back of the head.

According to one embodiment, the interior cover 100 has a pair of positioning protrusions 123 in the cover portion 120, and the substrate 300 can be positioned on the outer surface 112 of the interior cover 100 by the positioning protrusions 123. The positioning protrusions 123 protrude from the outer surface 112 of the interior cover, and are disposed in the vicinity of an upper end of the interior cover in the state of being spaced apart from each other. Further, the interior cover 100 may have a cushion member 150 which is disposed at each of the positioning protrusions. When the cap device 10 is worn on the scalp, the cushion member 150 makes contact with a top portion of the scalp and can provide a cushion feel to the user.

The exterior cover coupled to the interior cover is described with reference to FIGS. 1 to 3.

The exterior cover 200 may be formed by injection molding from an opaque plastic material. Screws are fastened to the exterior cover through the above-described through holes of the interior cover, and the interior cover 100 and the exterior cover 200 can be coupled to each other thereby. Alternatively, the exterior cover 200 and the interior cover 100 may be coupled to each other through fitting of female and male fitting elements.

The exterior cover 200 has a cover portion 220 covering the interior cover 100, and a brim portion 230 protruding from the cover portion 120 in the frontward direction FD. The cover portion 220 is formed in a substantially hemispherical shape so as to have a dimension larger than the cover portion 120 of the interior cover. The brim portion 230 has a shape corresponding to the brim portion 140 of the interior cover. In the coupled inner and exterior covers, the brim portion 140 of the interior cover and the brim portion 230 of the exterior cover are overlapped vertically and can be recognized by the user as a brim of the cap device.

The exterior cover 200 has a vent hole 211 for sucking air from the outside. The vent hole 211 is formed at an upper end of the exterior cover 200 and is located immediately above the blower 400. In one embodiment, an oblong slit 221 is formed in the frontward direction and the rearward direction in the cover portion 220 of the exterior cover. A mesh body 210 in which a plurality of vent holes 211 are formed is coupled to the slit 221, and the mesh body 210 has a shape corresponding to the slit 221. The mesh body 210 is made of a metal material. Therefore, the mesh body 210 can provide a color sense and a texture sense, which contrast with the exterior cover 200 made of an opaque plastic material, to the user.

The exterior cover 200 forms a passage, through which air emitted from the blower 400 flows, inside the cap device 10. That is, the exterior cover 200 coupled to the interior cover 100 is configured to define an air flow passage 240 along the outer surface 112 of the interior cover. The cover portion 220 of the exterior cover is formed in a hemispherical shape so as to have a dimension larger than the cover portion 120 of the interior cover, and therefore the air flow passage 240 can be defined between the inner surface of the exterior cover 200 and the outer surface of the interior cover 100.

The air emitted from the blower 400 can flow through the air flow passage 240 while diffusing from the upper end of the interior cover 100 toward the lower end of the interior cover 100. The air flow passage 240 defined between the interior cover 100 and the exterior cover 200 substantially takes a dome shape. Further, as shown in FIG. 3, according to one embodiment, the air flow passage 240 is formed so as to gradually narrow from the upper end of the interior cover 100 toward the lower end of the interior cover 100. That is, the cover portion 120 of the interior cover and the cover portion 220 of the exterior cover are configured such that the air flow passage 240 gradually narrows from the upper end of the interior cover toward the lower end of the interior cover. Due to such a shape characteristic of the air flow passage 240, the air emitted from the blower 400 can be emitted from the emitting holes 121 with strong pressure at a position distant from the blower 400.

The cap device according to one embodiment includes a plurality of diodes that irradiate light to the scalp. The light irradiated by the diodes promotes the repair and regeneration of scalp tissues and activates the cell activity of the scalp tissues. The diodes are mounted on the substrate 300 and are disposed in the air flow passage 240 between the interior cover 100 and the exterior cover 200 by the substrate 300. Referring to FIG. 3, the substrate 300 is disposed in the air flow passage 240 and may be coupled to the interior cover 100 to cover the outer surface 112 of the interior cover 100.

Figure 5:
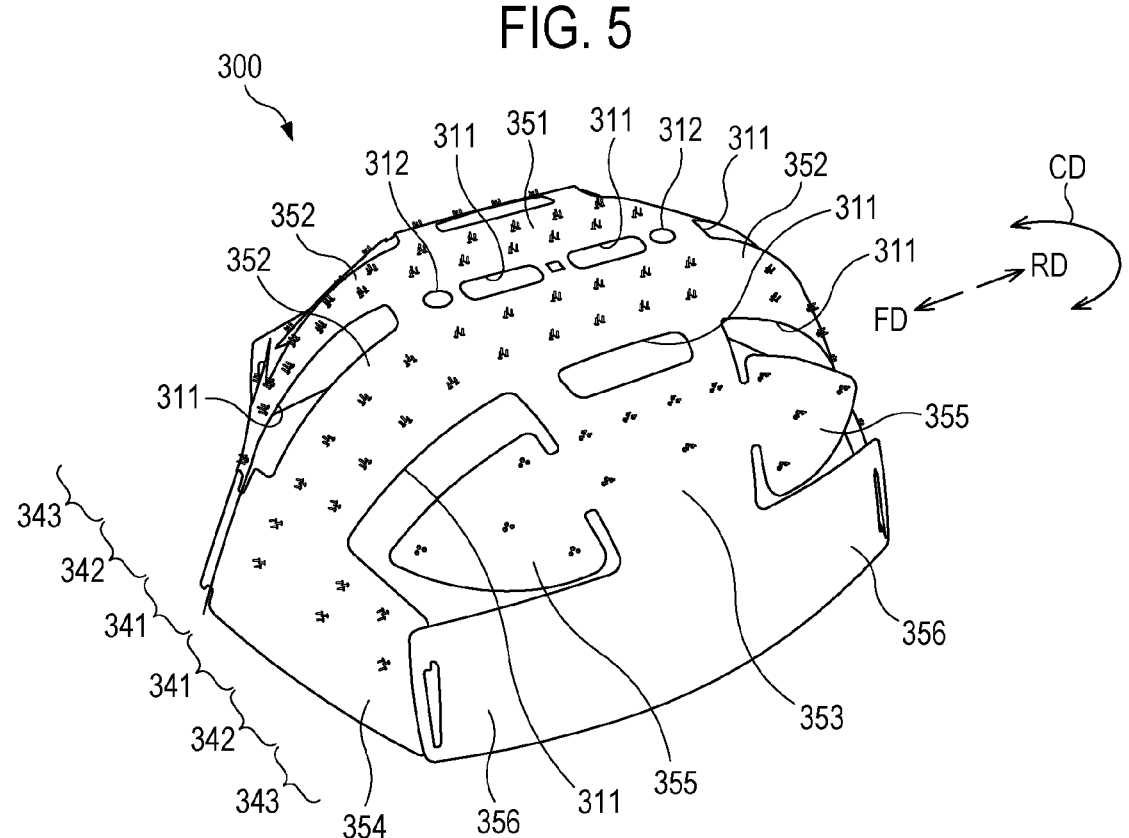
FIG. 5 is a perspective view showing a substrate of the cap device according to one embodiment.
Figure 6:
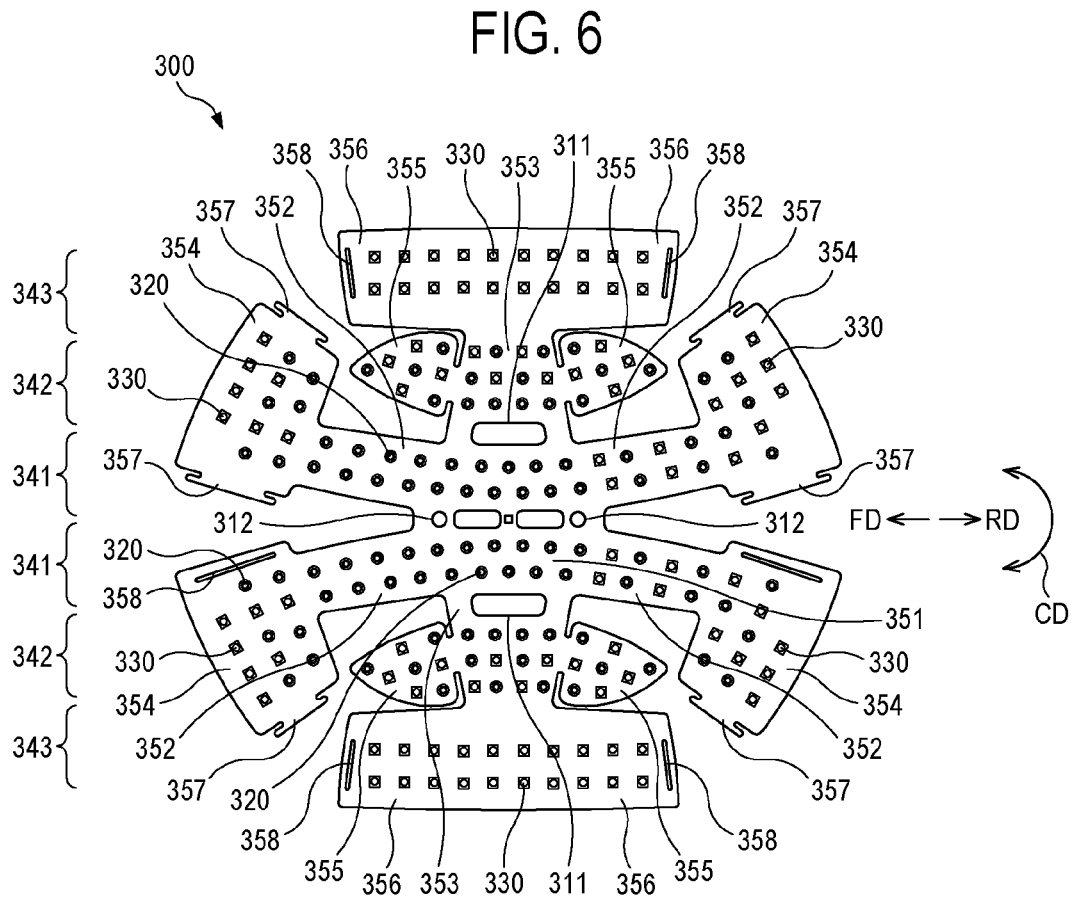
FIG. 6 is a plan view showing a flat plate form of the substrate shown in FIG. 5.

FIG. 5 is a perspective view showing the substrate of the cap device according to one embodiment, and FIG. 6 is a plan view showing a flat plate form of the substrate. Reference is made to FIGS. 3, 5, and 6.

As shown in FIG. 5, the substrate 300 disposed in the air flow passage takes a dome shape. The substrate 300 may be composed of a printed circuit board. The substrate 300 has a plurality of through holes 311 corresponding to the emitting holes 121 of the interior cover (see FIG. 4). The substrate 300 has positioning holes 312 in the vicinity of the upper end thereof. As shown in FIG. 3, when the substrate 300 is coupled to the interior cover 100 to cover the outer surface of the interior cover, some of the protruding portions 122 of the interior cover are inserted to the through holes 311, and the positioning protrusions 123 of the interior cover are inserted and fitted to the positioning holes 312, respectively. By the positioning protrusions 123 and the positioning holes 312, the substrate 300 can be disposed at a correct position on the outer surface 112 of the interior cover.

According to one embodiment, the substrate 300 is configured to be deformed from a flat plate shape to a dome form, and may be coupled to the interior cover to cover the outer surface of the interior cover in the state of being deformed into the dome form.

The substrate 300 has a plurality of laser diodes 320 and a plurality of infrared ray and red light emitting diodes 330 as the aforementioned diodes. Laser diodes, which are capable of irradiating laser light having a wavelength of about 650 nm to 655 nm and have an optical output of about 4 MW, may be used as the laser diodes 320. Light emitting diodes, which are capable of irradiating red light having a wavelength of 620 nm to 630 nm and infrared ray light having a wavelength of 840 nm to 860 nm and have a viewing angle of 120 degrees, may be used as the infrared ray and red light emitting diodes 330. The lights from the laser diodes 320 and the infrared ray and red light emitting diodes 330 are transmitted to the scalp. Thus, capillary vessels of the scalp tissues can be dilated, a blood flow rate and an amount of oxygen can be increased, hair follicle creation can be promoted, and hair roots can be strengthened.

The laser diodes 320 and the infrared ray and red light emitting diodes 330 are disposed in predetermined sections of the substrate 300. Specifically, the substrate 300 deformed into the dome form may be divided into a pair of first sections 341 disposed in the frontward direction FD and the rearward direction RD along the crown of a head, a pair of second sections 342 disposed to be spaced apart from the first sections 341 toward lateral ends of the substrate, and a pair of third sections 343 disposed to be spaced apart from the second sections 342 toward the laterals ends of the substrate. The laser diodes 320 may be installed in the pair of first sections 341 and the pair of second sections 342. Since the first sections 341 are placed on the forehead and crown of the head, the laser diodes 320 can be disposed on a portion of the scalp where significant hair loss occurs. The infrared ray and red light emitting diodes 330 may be installed mainly in the pair of third sections 343, and may be installed in the vicinity of the end portions of the first sections 341, and in the second sections 342.

The substrate 300 can be deformed from the flat plate form to the dome form. Accordingly, since the substrate, which is in the flat plate form where the above-described diodes are installed, is deformed into the dome form and can be installed on the interior cover, the substrate having the dome form, which has diodes and is disposed on the outer surface of the interior cover, can be easily manufactured. For deformation into the dome form, the substrate 300 is configured such that a portion thereof is bent toward the interior cover.

The substrate 300 includes a base portion 351, and a plurality of arm portions 352 and 353 extending from the base portion 351 and bendable toward the interior cover. The base portion 351 is positioned on the upper end of the interior cover, and the positioning holes 312 are formed in the base portion 351. The base portion 351 may be arcuately bent so as to correspond to a curvature of the outer surface of the interior cover. As shown in FIG. 6, the plurality of arm portions 352 and 353 extend radially from the base portion 351. Four first arm portions 352 may constitute the above-described first sections 341. The first arm portions 352 extend from the base portion 351 in the frontward direction and the rearward direction. Each first arm portion 352 has, at its end portion, a first coupling portion 354 that protrudes in a circumferential direction CD of the interior cover. Two second arm portions 353 extend from the base portion 351 in a lateral direction directed to the ear of the head. A pair of protruding portions 355 protruding in the frontward direction or the rearward direction are formed in each second arm portion 353. The protruding portions 355 of each second arm portion 353 and a portion of the second arm portion adjacent to the protruding portions 355 may constitute the second section 342. Each second arm portion 353 has, at its end portion, a pair of second coupling portions 356 protruding in the circumferential direction CD of the interior cover. The second coupling portions of each second arm portion may constitute the third section 343.

In the substrate 300, the arm portions, which are neighboring in the circumferential direction CD of the interior cover among the above-described plurality of arm portions, are formed to define one through hole among the plurality of through holes. For example, a pair of the first arm portions 352 neighboring in the circumferential direction are formed to define the through hole 311 therebetween, and the first arm portion 352 and the second arm portion 353 neighboring in the circumferential direction are formed to define the through hole 311 therebetween. Further, in the substrate 300, neighboring arm portions are configured to be separably coupled to each other. For coupling the arm portions, one of the first coupling portion 354 and the second coupling portion 356 may be provided with an engagement hook 357 protruding in a direction orthogonal to the circumferential direction of the interior cover, and the other of the first coupling portion 354 and the second coupling portion 356 may be provided with an engagement slit 358 into which the engagement hook 357 is fitted. As the engagement hook 357 is fitted to the engagement slit 358, the first coupling portions 354 of the first arm portions neighboring in the circumferential direction can be separably coupled to each other, and the first coupling portion 354 of the first arm portion and the second coupling portion 356 of the second arm portion neighboring in the circumferential direction can be separably coupled to each other. Therefore, the coupling portions of the neighboring arm portions are coupled in the circumferential direction, and the shape of the substrate 300 deformed into the dome form can be maintained thereby.

Figure 7:
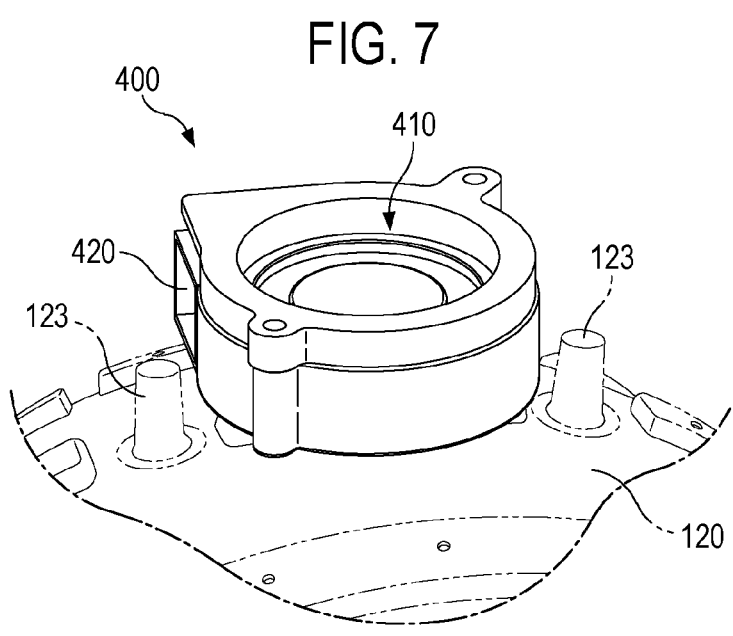
FIG. 7 is a perspective view showing a blower of the cap device for scalp care according to one embodiment.

FIG. 7 is a perspective view showing the blower according to one embodiment. Referring to FIGS. 3 and 7, the blower 400 is disposed in the air flow passage 240 so as to communicate with the air flow passage 240. Further, the blower 400 is disposed at the position of the upper end of the interior cover 100, and is disposed between the pair of positioning protrusions 123 of the interior cover 100. Therefore, the blower 400 is disposed substantially at the middle of the outer surface 112 of the interior cover, and can supply and blow the air in the form of wind to the whole area of the outer surface 112 of the interior cover. The blower 400 may be fixed to the inner surface of the exterior cover 200 by screws.

The blower 400 is configured to suck air through the vent hole 211 of the exterior cover. The blower 400 is positioned such that an air inlet 410 of the blower faces the vent hole 211. The blower 400 may include, inside thereof, a blowing fan that pressurizes the sucked air and converts the sucked air into the air in the form of wind having a fast flow velocity. The blower 400 may discharge the air converted into the form of wind through a blowing outlet 420. The blower 400 may have the air outlet 420 at one side thereof, may have two air outlets 420 spaced apart in the frontward direction and the rearward direction, or may have a plurality of air outlets 420 in a circumferential direction of the blower. The air in the form of wind emitted by the blower 400 enters the emitting holes 121 through the air flow passage 240, and can be emitted and supplied from the emitting holes 121 toward the scalp. As such, the blower 400 is configured to emit the air to the scalp through the emitting holes 121 via the air flow passage 240. The air emitted by the blower 400 through the emitting holes 121 is supplied to the scalp, thereby removing the heat applied to the scalp and cooling the scalp. The protruding portions 122 of the interior cover are arranged in three rows, the above-described first sections of the substrate 300 are disposed between the rows formed by the protruding portions 122, and the emitting holes 121 are formed in the protruding portions 122. Accordingly, a portion of the scalp, to which the laser light irradiated by the above-described laser diodes applies the heat, can be easily cooled by the air in the form of wind from the blower 400. Therefore, the heat of the crown portion of the scalp, which can become the cause of hair loss, can be removed. Since the blower 400 is located at the upper end of the interior cover 100, the air from the blower 400 can be emitted to the crown portion of the scalp with strong pressure in the range of a shortened flow distance.

Figure 8:
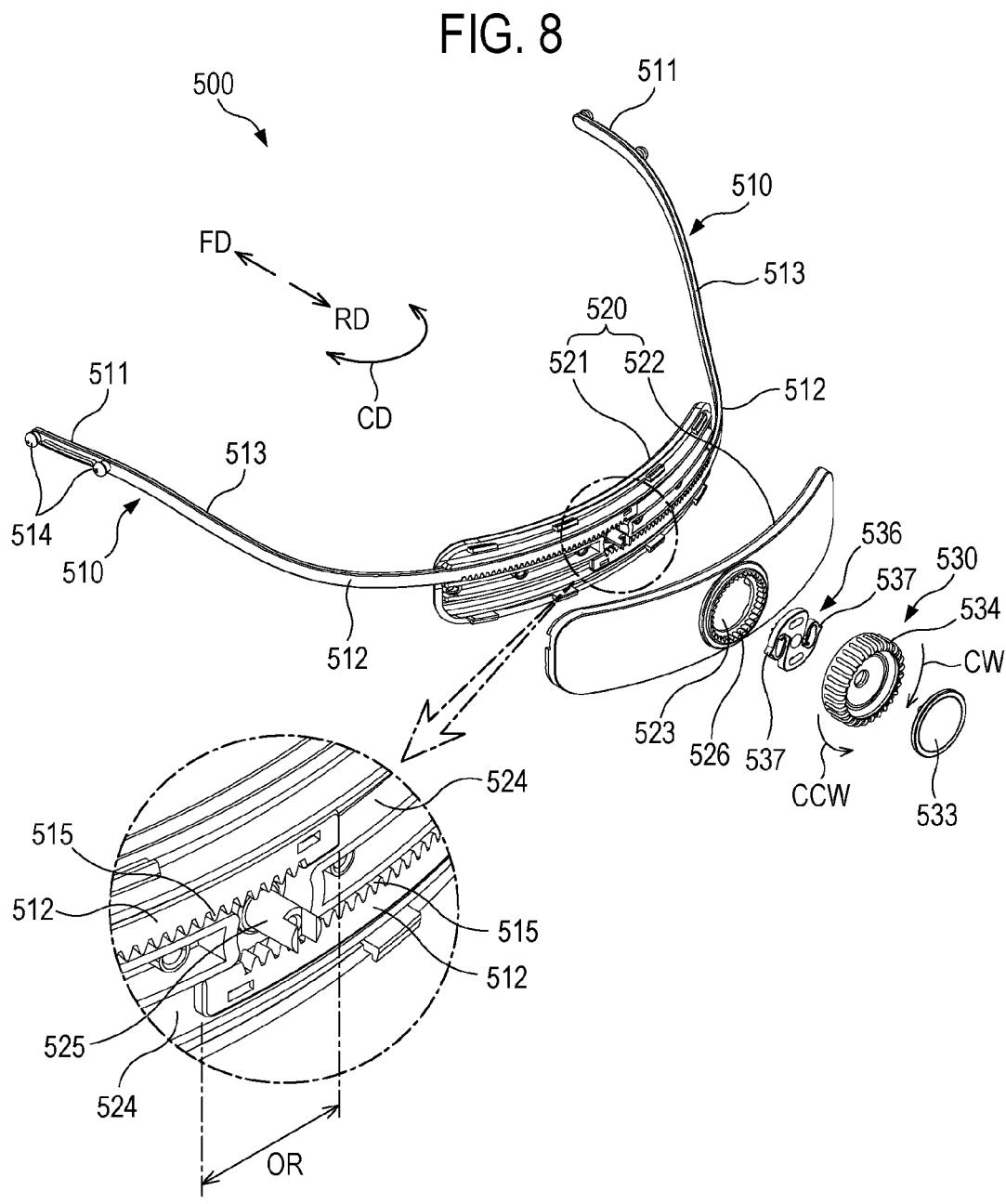
FIG. 8 is an exploded perspective view showing a gap adjustment device of the cap device for scalp care according to one embodiment.
Figure 9:
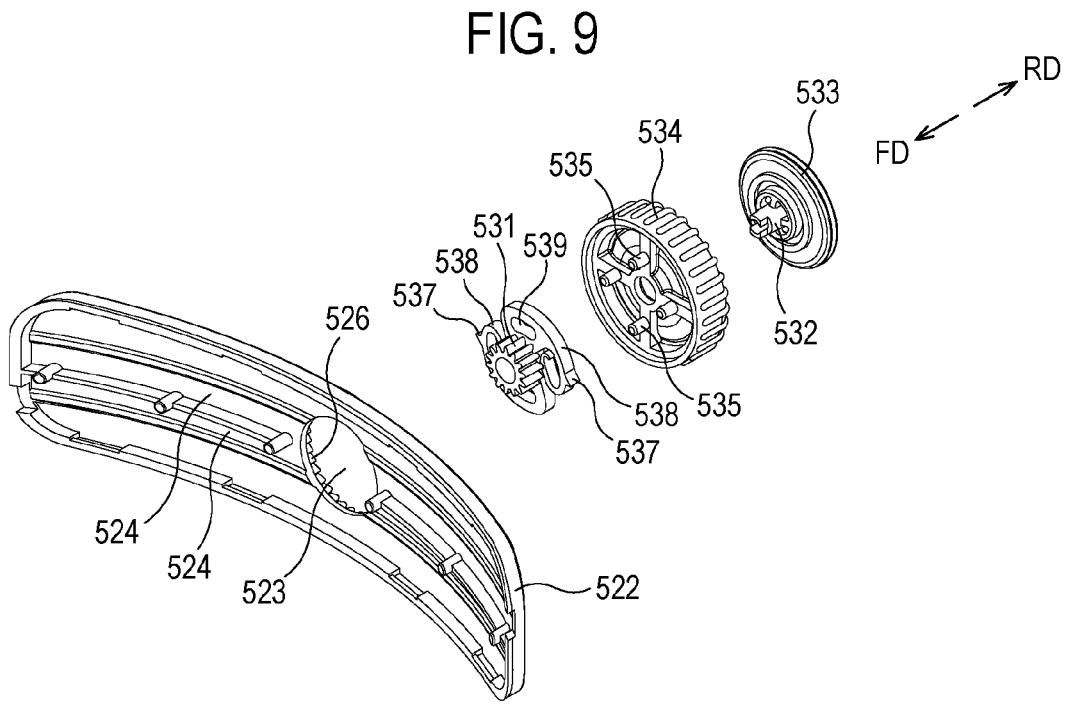
FIG. 9 is an exploded perspective view showing some components of the gap adjustment device shown in FIG. 8.
Figure 10:
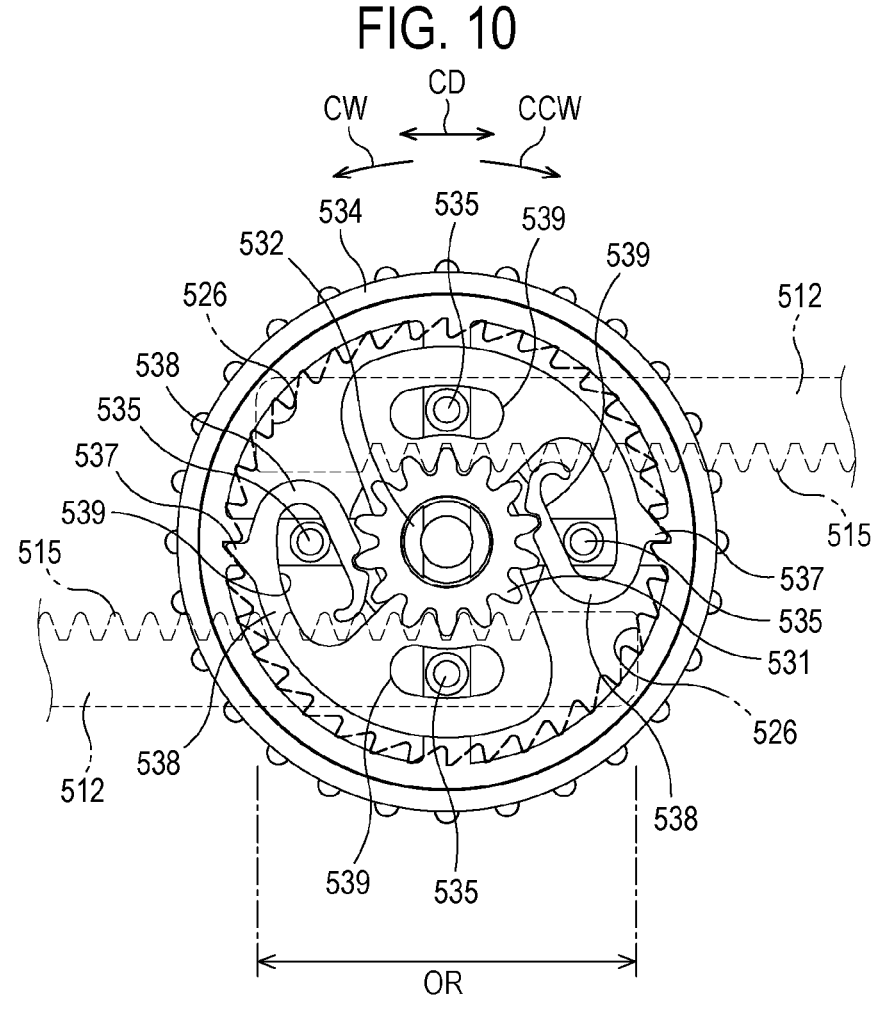
FIG. 10 is a front view showing a state where some components of the gap adjustment device shown in FIG. 8 are assembled.

The cap device according to one embodiment can be applied to various head sizes of users, and therefore the cap device can increase user convenience. To this end, the cap device according to one embodiment may include a gap adjustment device which can adjust a gap between the inside of the cap device and the scalp of the head. FIG. 8 is an exploded perspective view showing the gap adjustment device of the cap device according to one embodiment. FIG. 9 is an exploded perspective view showing some components of the gap adjustment device shown in FIG. 8, and FIG. 10 is a front view showing a state where some components of the gap adjustment device shown in FIG. 8 are assembled. The gap adjustment device is described with reference to FIGS. 2 and 8 to 10.

The cap device 10 may include a gap adjustment device 500 coupled to the interior cover 100. The gap adjustment device 500 may be disposed at a position spaced apart from the brim portions 140 and 230 of the inner and exterior covers in the rearward direction RD. That is, the gap adjustment device 500 is configured to adjust the gap between the interior cover 100 and the scalp in the frontward direction FD and the rearward direction RD of the head. Further, the gap adjustment device 500 is configured to adjust the gap in such a way that the user rotates a dial. Therefore, as the user manipulates the gap adjustment device 500, the gap between the inner surface 111 of the interior cover 100 and the scalp can be adjusted, and the cap device according to one embodiment can be applied to all users having relatively large or small head sizes.

The gap adjustment device 500 includes a pair of bands 510 for fixing to the interior cover 100, a housing 520 in which the pair of bands 510 are inserted and accommodated and which is brought into contact with the back of a user's head, and an adjustment dial 530 rotatably coupled to the housing 520.

The pair of bands 510 are disposed in the circumferential direction CD of the interior cover 100, and are located to partially overlap with each other in the circumferential direction. When the adjustment dial 530 is rotated, an overlapping region OR of the pair of bands 510 can be increased or reduced. Therefore, the housing 520 can be moved in the frontward direction FD or the rearward direction RD, and the gap between the interior cover 100 and the scalp can be adjusted in the frontward direction FD or the rearward direction RD.

Each band 510 may be made of a plastic material. Each band 510 has one end portion 511 removably coupled to the inner surface 111 of the interior cover, an opposite end portion 512 inserted into and accommodated in the housing 520, and a connection portion 513 interconnecting the one end portion 511 and the opposite end portion 512. The one end portion 511 is formed with a pair of fitting protrusions 514 protruding toward the inner surface 111 of the interior cover, and the interior cover 100 has, in the vicinity of the lower end thereof, fitting holes 132 into which the fitting protrusions 514 are fitted (see FIG. 4). Since the fitting protrusions 514 are fitted into the fitting holes 132, the one end portion 511 of the band 510 can be removably coupled to the inner surface 111 of the interior cover. The opposite end portion 512 is formed with a rack gear 515. The one end portion 511 is located in parallel to the lower end of the interior cover 100. The connection portion 513 is inclined such that the one end portion 511 and the opposite end portion 512 are located at different heights. Therefore, the housing 520 accommodating the opposite end portion 512 can be disposed below the lower end of the interior cover 100 at the rear side of the interior cover 100.

As the overlapping region OR of the pair of bands 510 is increased or reduced, the housing 520 can be moved in the frontward direction FD or the rearward direction RD, and a distance between a front end of interior cover 100 and the housing 520 can be decreased or increased. The housing 520 is configured to accommodate the opposite end portions 512 of the pair of bands 510 such that the opposite end portions are slidable in opposite directions. The housing 520 includes a front housing 521 arcuately bent so as to be in contact with the back of a head, and a rear housing 522 separably coupled to the front housing 521 and formed with a dial hole 523 in which the adjustment dial 530 is disposed.

A pair of slide grooves 524 are formed in the front housing 521 and the rear housing 522 in the circumferential direction CD of the interior cover. The pair of slide grooves 524 are vertically spaced apart from each other, and each slide groove extends from a lateral end of the housing 520 to the inside of the housing 520. Since the opposite end portion 512 of each band 510 is inserted to and accommodated in the slide groove 524, the housing 520 accommodates the opposite end portions 512 so that the opposite end portions are slidable in the opposite directions. The front housing 521 has, in its middle, a dial shaft 525 that protrudes rearward between the pair of slide grooves 524. The dial hole 523 is formed in the middle of the rear housing 522 and is perforated through the rear housing 522. The rear housing 522 has, on its rear surface, a plurality of detent teeth 526 surrounding the dial hole 523. The plurality of detent teeth 526 are disposed in an annular shape about a rotation axis of the adjustment dial 530.

As the adjustment dial 530 is rotated in a clockwise direction, the overlapping region of the pair of bands 510 are increased and the housing 520 can be moved in the front-ward direction FD. As the adjustment dial 530 is rotated in a counterclockwise direction, the overlapping region of the pair of bands 510 are reduced and the housing 520 can be moved in the rearward direction RD. The adjustment dial 530 is rotatably coupled to the front housing 521 through the rear housing 522. The adjustment dial 530 has a pinion gear 531 located inside the housing 520. The pinion gear 531 is disposed between the rack gears 515 of respective opposite end portions 512 of the pair of bands 510, and meshes with the rack gears 515. The pinion gear 531 is rotated by the rotation of the adjustment dial 530, and the rack gears 515 meshing with the pinion gear 531 are moved in opposite directions. Therefore, the overlapping region OR of the pair of bands 510 are increased or reduced.

Further, the adjustment dial 530 may be configured to move the rack gears 515 by a predetermined fine interval and to stop the rack gears 515. Referring to FIGS. 8 to 10, the adjustment dial 530 includes an attachment shaft 532 for attaching the adjustment dial 530 to the housing 520, a dial wheel 534 rotatable about the attachment shaft 532, and a ratchet plate 536 that moves in conjunction with the rotation of the dial wheel 534. The pinion gear 531 may be formed integrally with the ratchet plate 536 or may be separably coupled to the ratchet plate 536.

The attachment shaft 532 passes through the dial wheel 534, the ratchet plate 536, the pinion gear 531, and the dial hole 523, and may be coupled to the dial shaft 525 by a screw. The attachment shaft 532 has a flange 533, and the flange 533 can prevent the separation of the dial wheel 534. The dial wheel 534 can be rotated about the dial shaft 525 and the attachment shaft 532 in the clockwise direction CW and the counterclockwise direction CCW. The dial wheel 534 has ratchet rotating protrusions 535 protruding in the frontward direction FD. The ratchet plate 536 is covered by the dial wheel 534 and is located inside the annular shape formed by the detent teeth 526.

The ratchet plate 536 has a pair of ratchet teeth 537 each of which meshes with one of the detent teeth 526, and a pair of elastic arms 538 enabling the ratchet teeth 537 to be moved in a radially outward direction and a radially inward direction. Further, slits 539 are formed in and perforated through the ratchet plate 536, and the ratchet rotating protrusions 535 are inserted to the slits, respectively, with a clearance. The slit 539 is formed in a circular arc shape so as to correspond to the rotation direction of the dial wheel 534, and has a length greater than a width of the ratchet rotating protrusion 535. That is, in the state where the ratchet rotating protrusion 535 is inserted to the slit 539, a clearance space is formed between the ratchet rotating protrusion 535 and the slit 539 in the rotation direction of the dial wheel. Further, the elastic arm 538 is bent approximately in a U shape, thereby defining the slit 539 therein. The ratchet rotating protrusion 535 can come into contact with an inner surface of the elastic arm 538. An inward half of the elastic arm 538 is disposed obliquely with respect to a movement direction of the ratchet rotating protrusion 535. For example, when the dial wheel 534 is rotated in the counterclockwise direction, the elastic arm 538 can make contact with the ratchet rotating protrusion 535 so as to be deformed in the radially inward direction by the ratchet rotating protrusion 535.

Referring to FIG. 10, as the dial wheel 534 is rotated, the ratchet rotating protrusion 535 comes into contact with an end of the slit 539. As the dial wheel 534 is rotated in the state where the ratchet rotating protrusion 535 is in contact with the end of the slit 539, the ratchet plate 536 and the pinion gear 531 are rotated. By the rotation of the pinion gear 531, the rack gears 515 can be moved. Further, as the dial wheel 534 is rotated in the state where the ratchet rotating protrusion 535 is in contact with the end of the slit 539, the ratchet tooth 537 of the ratchet plate 536 is disengaged from one detent tooth 526 and then meshes with another detent tooth 526 adjacent to the one detent tooth. For example, as the dial wheel 534 is rotated in the clockwise direction CW, the ratchet tooth 537 can sequentially mesh with the detent teeth 526 while being rotated in the clock-wise direction. Since the detent tooth 526 takes a wedge shape, the ratchet tooth 537 can sequentially mesh with the detent teeth 526 in accordance with the rotation of the dial wheel 534 in the clockwise direction CW. As the dial wheel 534 is rotated in the clockwise direction CW, the pinion gear 531 is rotated in the clockwise direction CW, the overlap-ping region OR of the pair of bands is increased, and the housing can be moved in the frontward direction. When the dial wheel 534 is rotated in the counterclockwise direction CCW, the ratchet rotating protrusion 535 comes into contact with the elastic arm 538 and pushes the elastic arm 538 in the radially inward direction, and therefore, the ratchet tooth 537 can be disengaged from the detent tooth 526. Thereafter, as the dial wheel 534 is further rotated in the counterclockwise direction CCW, the pinion gear 531 is rotated in the counterclockwise direction, the overlapping region OR of the pair of bands is reduced, and the housing can be moved in the rearward direction.

Since the pinion gear 531 and the ratchet plate 536 are coupled to each other and the ratchet plate 536 sequentially meshes with the plurality of detent teeth 526 one by one, a rotation amount of the pinion gear 531 can be adjusted by a range equal to a pitch between neighboring detent teeth 526. Therefore, the user can finely adjust the increase or decrease of the overlapping region of the pair of bands 510 by a unit of the pitch of the detent teeth 526. Further, since the rotation of the pinion gear 531 can be fixed in the state where the ratchet tooth 537 of the ratchet plate meshes with the detent tooth 526, the overlapping region OR of the pair of bands 510 can be fixed, a braking action can be applied to the pair of bands 510, and the position of the housing 520 can be fixed. Further, since the clearance space is formed between the ratchet rotating protrusion 535 of the dial wheel and the slit 539 of the ratchet plate, the pinion gear 531 is not rotated immediately by the rotation of the dial wheel 534, and a rotational delay allowed by the clearance space can occur. Therefore, the user can rotate the dial wheel 534 with a clearance feel, and can have a better manipulation feel for the dial wheel.

Figure 11:
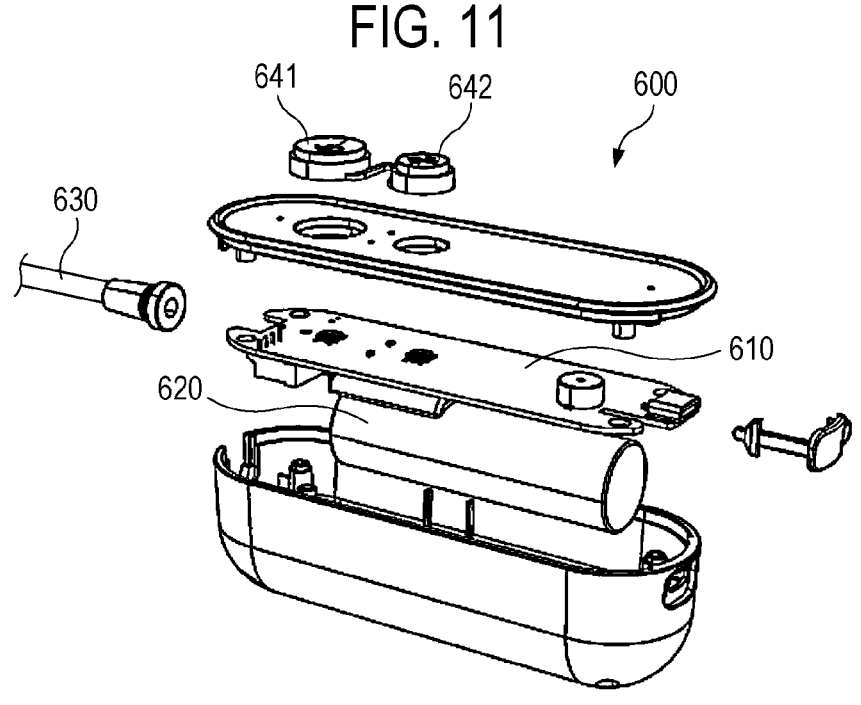
FIG. 11 is an exploded perspective view showing a control device and an electrical power source of the cap device for scalp care according to one embodiment.

The cap device according to one embodiment is configured to be portable, and therefore, the user can use the cap device regardless of the location of electrical power for driving the components of the cap device. Further, the cap device according to one embodiment is configured to allow the user to selectively operate the diodes for irradiating light for scalp care and the blower for providing air to the scalp. In this regard, the cap device according to one embodiment includes a control device configured to control the operations of the diodes and the blower, and an electrical power source supplying electrical power to the diodes and the blower. The control device and the electrical power source may be installed in a manipulator electrically connected to the substrate. FIG. 11 is an exploded perspective view showing a control device and an electrical power source of the cap device according to one embodiment. The operation of the cap device according to one embodiment is described with reference to FIGS. 1 and 11.

The cap device according to one embodiment includes a control device 610 and an electrical power source 620. The control device 610 and the electrical power source 620 may be installed inside a manipulator 600, which is connected to an electric wire 630 extending from the exterior cover 200. The electric wire 630 is electrically connected to the control device 610 and the electrical power source 620, and is electrically connected to the substrate and the blower located in the air flow passage.

The electrical power source 620 is configured to supply electric power to the laser diodes, the infrared ray and red light-emitting diodes, and the blower. The electrical power source 620 may include, but is not limited to, a rechargeable battery. The electrical power source 620 is electrically connected to the control device 610.

The control device 610 is configured to control the operation of the laser diodes, the operation of the infrared ray and red light emitting diodes, and the operation of the blower. The control device 610 may include a circuit board and a processor mounted on the circuit board. Further, the circuit board may be provided with a timer element that is operated in conjunction with the processor.

The control device 610 may be configured to operate or deactivate the laser diodes and the infrared ray and red light emitting diodes in response to the user's input. In this regard, the manipulator 600 includes a first push button 641 which the user can push for the operation of the diodes. Further, the control device 610 may be configured to operate or deactivate the blower in response to the user's input. In this regard, the manipulator 600 includes a second push button 642 which the user can push for the operation of the blower.

In the state where the cap device according to one embodiment is worn on the user's scalp, the user may push the first push button 641. Therefore, the control device 610 may operate the laser diodes and the infrared ray and red light emitting diodes. When the user pushes the first push button 641 again, the control device 610 may deactivate the laser diodes and the infrared ray and red light emitting diodes. In case where the circuit board is provided with the timer element, the control device 610 may operate the diodes for a predetermined time (e.g., about 15 minutes) after manipulation of the first push button 641, and thereafter may deactivate the diodes. When the user pushes the second push button 642, the control device 610 may operate the blower. That is, the blower may be selectively operated by the user. When the user pushes the second push button 642 again, the control device 610 may deactivate the blower. Alternatively, in case where the circuit board is provided with the timer element, the control device 610 may operate the blower for a predetermined time after manipulation of the second push button 642, and thereafter may deactivate the blower.

As another example of operation, the control device 610 may be configured to interlink the operations of the diodes and the blower. For example, the control device 610 may be configured to operate the diodes and the blower simultaneously or sequentially when the user pushes the first push button 641. As a further example of operation, the control device 610 may be configured to increase or decrease the output of the blower in response to the user's input. For example, in the state where the diodes are being operated, the output of the blower may be increased or decreased by the control device 610.

The user may remove the cap device according to one embodiment from the scalp in the state where the diodes are deactivated. Or, frequently, the user may remove the cap device according to one embodiment from the scalp in the state where the diodes are being operated. In such a case, the laser light or the infrared ray light irradiated by the diodes may adversely affect the user's eyes. The cap device according to one embodiment is configured so that the diodes are operated only in the state where the user is wearing the cap device. In this regard, the cap device according to one embodiment may include a wearing detection sensor that provides information of a wearing state to the control device.

Referring to FIGS. 2 and 3, the cap device according to one embodiment includes a wearing detection sensor 160 disposed in the interior cover 100. The wearing detection sensor 160 may be disposed in the interior cover 100 so as to face an inside space of the interior cover 100 through the interior cover 100 in the state of being mounted on the substrate 300. The wearing detection sensor 160 is electrically connected to the control device 610 shown in FIG. 11. The wearing detection sensor 160 is configured to detect the state where the interior cover 100 is worn on the scalp, and can transmit the detection result of the wearing state to the control device 610.

The control device 610 is configured to stop the operations of the laser diodes and the infrared ray and red light emitting diodes when the wearing detection sensor 160 detects that the scalp does not exist in the interior cover 100. Therefore, when the user removes the cap device from the scalp in the state where the diodes are being operated, the operation of the diodes may be stopped by the control device 610.

The wearing detection sensor 160 may be installed at the upper end of the interior cover 100 so as to correspond to the position of the crown of the scalp. One or more wearing detection sensors 160 may be installed in the interior cover 100. The wearing detection sensor 160 may include a photo reflective sensor. The wearing detection sensor 160 may be configured to receive the light irradiated by the infrared ray and red light emitting diodes through its light receiving portion and to transmit a light receiving signal to the control device 610. Further, when the wearing detection sensor does not receive the light from the infrared ray and red light emitting diodes, the wearing detection sensor 160 may be configured to transmit a signal of not receiving the light to the control device 610. Since the infrared ray and red light emitting diodes are disposed at the positon of a side surface of the wearer's head, the wearing state of the cap device can be detected by the wearing detection sensor 160 located at the upper end of the interior cover 100. When the signal from the wearing detection sensor 160 corresponds to the signal of not receiving light from the infrared ray and red light emitting diodes, the control device 610 may determine that the scalp exists in the interior cover 100 and the cap device is worn on the scalp. When the signal from the wearing detection sensor 160 corresponds to the signal of receiving light from the infrared ray and red light emitting diodes, the control device 610 may determine that the scalp does not exist in the interior cover 100.

The technical idea of the present disclosure has been described heretofore with reference to some embodiments and examples shown in the accompanying drawings. However, it is to be understood that various substitutions, modifications, and alterations may be made without departing from the technical idea and scope of the present disclosure that can be understood by those of ordinary skill in the technical field to which the present disclosure pertains. Further, it is to be understood that such substitutions, modifications, and alterations fall within the scope of the appended claims.

What is claimed is:

1. A cap device for scalp care wearable on a scalp of a head, comprising:
    an interior cover formed to cover the scalp and composed of a transparent material, the interior cover having a plurality of emitting holes for emitting air to the scalp;
    an exterior cover coupled to the interior cover and configured to define an air flow passage along an outer surface of the interior cover, the exterior cover having a vent hole for sucking air from an outside;
    a substrate coupled to the interior cover in the air flow passage to cover the outer surface of the interior cover, the substrate having a plurality of laser diodes and a plurality of infrared ray and red light emitting diodes, which irradiate light to the scalp, and a plurality of through holes positioned to be aligned with the plurality of emitting holes; and
    a blower disposed in a position of an upper end of the interior cover to communicate with the air flow passage, the blower being configured to suck air through the vent hole and to emit the air to the scalp through the plurality of emitting holes via the air flow passage.

2. The cap device for scalp care of claim 1, wherein the interior cover has a plurality of protruding portions protruding toward the exterior cover, and
    wherein at least a portion of the plurality of emitting holes are formed in and perforated through the plurality of protruding portions.

3. The cap device for scalp care of claim 2, wherein the plurality of protruding portions are arranged in a plurality of rows in the interior cover.

4. The cap device for scalp care of claim 1, wherein the interior cover has a pair of positioning protrusions protruding from the outer surface in a vicinity of the upper end,
    wherein the substrate has positioning holes to which the pair of positioning protrusions are fitted respectively, and
    wherein the blower is disposed between the pair of positioning protrusions.

5. The cap device for scalp care of claim 1, wherein the interior cover and the exterior cover are configured such that the air flow passage gradually narrows from the upper end of the interior cover toward a lower end of the interior cover.

6. The cap device for scalp care of claim 1, wherein each of the interior cover and the exterior cover has a brim portion protruding in a frontward direction of the head, and wherein the brim portion of the interior cover and the brim portion of the exterior cover have a corresponding shape.

7. The cap device for scalp care of claim 1, wherein the substrate includes a base portion positioned on the upper end of the interior cover, and a plurality of arm portions extending from the base portion and bendable toward the interior cover,
    wherein the arm portions, which are neighboring in a circumferential direction of the interior cover among the plurality of arm portions, are formed to define one through hole among the plurality of through holes, and
    wherein the neighboring arm portions are configured to be separably coupled to each other.

8. The cap device for scalp care of claim 1, further comprising a gap adjustment device including at least one band coupled to the interior cover and a housing configured to move relative to the interior cover, the gap adjustment device being configured to adjust a gap between the interior cover and the scalp in a frontward direction and a rearward direction of the head.

9. The cap device for scalp care of claim 8, wherein the gap adjustment device includes:
    the at least one band including a pair of bands each having one end portion removably coupled to the interior cover and an opposite end portion formed with a rack gear, the pair of bands being disposed in a circumferential direction of the interior cover;
    the housing configured to accommodate the opposite end portions of the pair of bands such that the opposite end portions are slidable in opposite directions, the housing configured to be in contact with a back of the head; and
    an adjustment dial rotatably coupled to the housing and having a pinion gear disposed between and meshing with the rack gears of the pair of bands.

10. The cap device for scalp care of claim 9, wherein the housing has a plurality of detent teeth disposed in an annular shape about a rotation axis of the adjustment dial,
    wherein the adjustment dial has a ratchet plate coupled to the pinion gear and having a ratchet tooth meshing with one of the detent teeth, and
    wherein the ratchet tooth sequentially meshes with the plurality of detent teeth as the adjustment dial is rotated.

11. The cap device for scalp care of claim 1, further comprising:

a control device configured to control an operation of the laser diodes, an operation of the infrared ray and red light emitting diodes, and an operation of the blower; and an electrical power source supplying electrical power to the laser diodes, the infrared ray and red light emitting diodes, and the blower.

12. The cap device for scalp care of claim 11, further comprising a wearing detection sensor disposed in the interior cover and configured to detect a state where the interior cover is worn on the scalp, wherein the control device is configured to stop the operations of the plurality of laser diodes and the plurality of infrared ray and red light emitting diodes when the wearing detection sensor detects that the scalp does not exist in the interior cover.

\* \* \* \* \*